United States Patent
Yoshida et al.

(10) Patent No.: US 8,237,127 B2
(45) Date of Patent: Aug. 7, 2012

(54) ELECTRONIC CASSETTE (75) Inventors: Yutaka Yoshida, Kanagawa (JP);
Yasunori Ohta, Kanagawa (JP);
Naoyuki Nishino, Kanagawa (JP); Keiji Tsubota, Kanagawa (JP); Takeshi Kamiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 12/478,782

(22) Filed: Jun. 5, 2009

(65) Prior Publication Data

US 2009/0309034 A1 Dec. 17, 2009

(30) Foreign Application Priority Data

Jun. 11, 2008 (JP) ................................. 2008-153163

(51) Int. Cl.
*G01T 1/24* (2006.01)

(52) U.S. Cl. .............. 250/370.09; 250/370.08; 378/169; 378/182; 378/189

(58) Field of Classification Search ............. 250/370.08, 250/370.09; 378/169, 182, 189
See application file for complete search history.

(56) References Cited

U.S. PATENT DOCUMENTS

| 6,805,484 | B2* | 10/2004 | Kuramoto et al. ............ 378/189 |
| 6,893,156 | B2* | 5/2005 | Sharpensteen et al. ....... 378/177 |
| 2002/0080921 | A1* | 6/2002 | Smith et al. ................... 378/189 |
| 2003/0047696 | A1* | 3/2003 | Brahm et al. .................. 250/584 |
| 2006/0023929 | A1* | 2/2006 | Luo et al. ....................... 382/132 |
| 2006/0097177 | A1* | 5/2006 | Yamamoto ............... 250/370.08 |
| 2006/0109958 | A1* | 5/2006 | Ertel et al. ..................... 378/205 |
| 2006/0113481 | A1* | 6/2006 | Murphy et al. .......... 250/370.09 |
| 2006/0256928 | A1* | 11/2006 | Grosse .......................... 378/189 |
| 2008/0069304 | A1* | 3/2008 | Muszak et al. ................ 378/114 |
| 2008/0095324 | A1* | 4/2008 | Watanabe ...................... 378/198 |
| 2008/0130837 | A1* | 6/2008 | Heath et al. ................... 378/205 |
| 2008/0240358 | A1* | 10/2008 | Utschig et al. ................ 378/107 |

FOREIGN PATENT DOCUMENTS

JP 2004-77641 3/2004

* cited by examiner

*Primary Examiner* — David Porta
*Assistant Examiner* — Djura Malevic
(74) *Attorney, Agent, or Firm* — SOLARIS Intellectual Property Group, PLLC (57) ABSTRACT

An electronic cassette has a casing that houses a radiation converter thereinside. The radiation converter detects radiation from a radiation source that has been transmitted through a subject, and converts the radiation into radiographic image information. Plural handles are disposed on the casing of the electronic cassette, so that a person can grip the plural handles and carry the electronic cassette. Thus, the person can grip and carry the electronic cassette while dispersing the weight of the electronic cassette, so carrying the electronic cassette becomes easy. Further, when the person loads the electronic cassette into a shooting table or the like, the person can grip either of the plural handles and load the electronic cassette. For this reason, handling of the electronic cassette becomes easy.

6 Claims, 13 Drawing Sheets

ELECTRONIC CASSETTE

CROSS-REFERENCE TO RELATED APPLICATION

This application claims priority under 35 USC 119 from Japanese Patent Application No. 2008-153163, the disclosure of which is incorporated by reference herein.

BACKGROUND OF THE INVENTION

1. Field of the Invention

The present invention relates to a portable electronic cassette.

2. Description of the Related Art

As an electronic cassette, the electronic cassette disclosed in Japanese Patent Application Laid-Open Publication (JP-A) No. 2004-77641 is publicly known. The electronic cassette of JP-A No. 2004-77641 is configured such that its handle can move in the electronic cassette and can be detached from the electronic cassette so that the handle does not get in the way when a person handling the electronic cassette loads the electronic cassette into a standing mount. Moreover, in the electronic cassette of JP-A No. 2004-77641, the handle is configured such that it can be used as a chin rest for an examinee who is standing to rest his/her chin on.

In this connection, when the detection region that detects the radiation is rectangular, it is necessary to know, depending on the purpose of imaging, whether to orient the electronic cassette vertically or horizontally when imaging an examinee who is standing, but in a configuration where the handle is disposed in one direction of the electronic cassette as in JP-A No. 2004-77641, loading the electronic cassette into a standing mount becomes difficult depending on the orientation in which the electronic cassette is to be loaded.

Further, when imaging an examinee who is lying down, sometimes the person handling the electronic cassette loads the electronic cassette such that its long sides are aligned with the longitudinal direction of the bed on which the examinee lies, and sometimes the person handling the electronic cassette loads the electronic cassette such that its short sides are aligned with the longitudinal direction of the bed on which the examinee lies, but loading the electronic cassette into the bed becomes difficult depending on the orientation in which the electronic cassette is to be loaded.

Meanwhile, from another standpoint, in JP-A No. 2004-77641, no consideration is given in regard to safely carrying a heavy cassette.

SUMMARY OF THE INVENTION

In consideration of the above-described circumstances, the present invention provides an electronic cassette whose handling becomes easy.

An electronic cassette pertaining to a first aspect of the invention includes: a casing; a radiation converter that is housed inside the casing, detects radiation from a radiation source that has been transmitted through a subject, and converts the radiation into radiographic image information; a control component that controls the radiation converter; a power supplying component that supplies electrical power to at least one of the radiation converter and the control component; and plural grip portions that are disposed on the casing.

According to the first aspect of the invention, the electronic cassette includes the radiation converter that is housed inside the casing, the control component and the power supplying component, and when a person carries a heavy electronic cassette, the person can grip the plural grip portions and carry the electronic cassette. For this reason, the person can carry the electronic cassette while dispersing the weight of the electronic cassette, so carrying the electronic cassette becomes easy.

Further, when the person loads the electronic cassette into a shooting table or the like, the person can grip either of the plural handles and load the electronic cassette.

In this manner, according to the first aspect of the invention, handling of the electronic cassette becomes easy In the electronic cassette pertaining to the first aspect of the invention, at least one of the plural grip portions is detachable.

According to this configuration, when a person handles the electronic cassette, the grip portion that is configured to be detachable can be removed when it is not needed, that grip portion does not get in the way, and handling of the electronic cassette becomes easy.

The electronic cassette pertaining to the first aspect of the invention may be configured to further include an attachment detecting component that detects whether or not the grip portion that is detachable is attached, wherein the control component changes, on the basis of the detection result that the attachment detecting component has detected, image processing of the radiographic image information that the radiation converter has converted.

According to this configuration, the image processing content of the radiographic image information that the radiation converter has converted changes depending on the attachment situation of the grip portions, so it becomes unnecessary to separately perform operation to change the image processing content of the image information.

In the electronic cassette pertaining to the first aspect of the invention, at least one of the control component and the power supplying component may be integrated with the grip portion that is detachable.

According to this configuration, at least one of the control component and the power supplying component is integrated with the grip portion that is detachable, so at least one of the control component and the power supplying component can be detached, and handling such as maintenance becomes easy.

The present invention is configured as described above, so handling of the electronic cassette becomes easy.

BRIEF DESCRIPTION OF THE DRAWINGS

An embodiment of the present invention will be described in detail based on the following figures, wherein.

DETAILED DESCRIPTION OF THE INVENTION

Below, an example of an embodiment pertaining to the present invention will be described on the basis of the drawings.

(Configuration of Electronic Cassette Pertaining to Present Embodiment)

Figure 1:
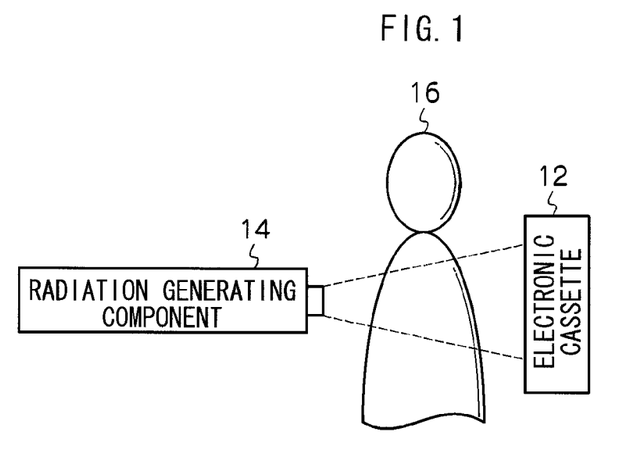
FIG. 1 is a general diagram showing the disposition of an electronic cassette during shooting of a radiographic image.
Figure 2:
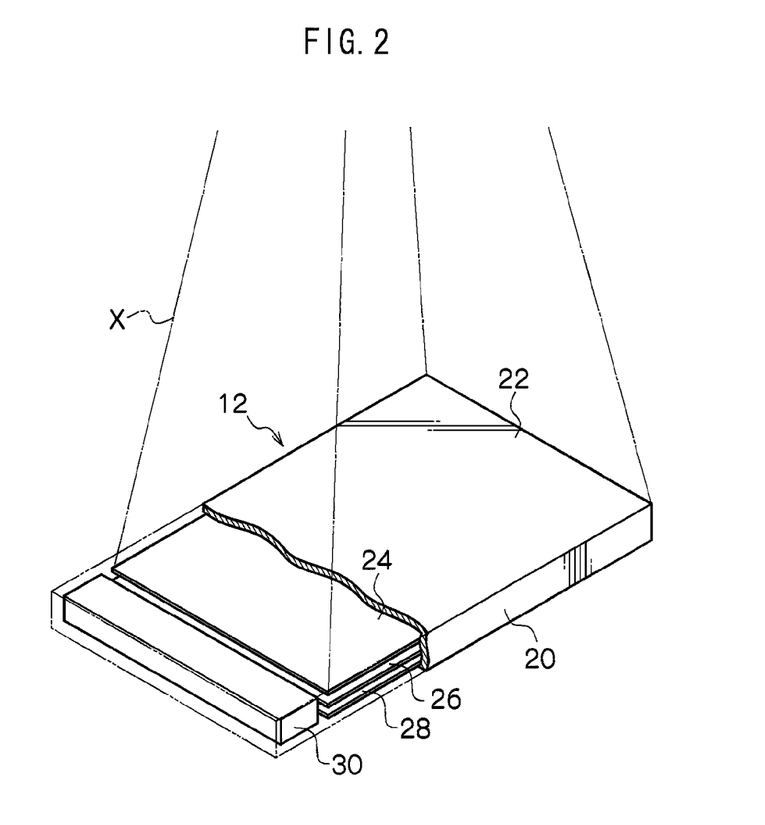
FIG. 2 is general perspective diagram showing the internal structure of the electronic cassette.
Figure 3:
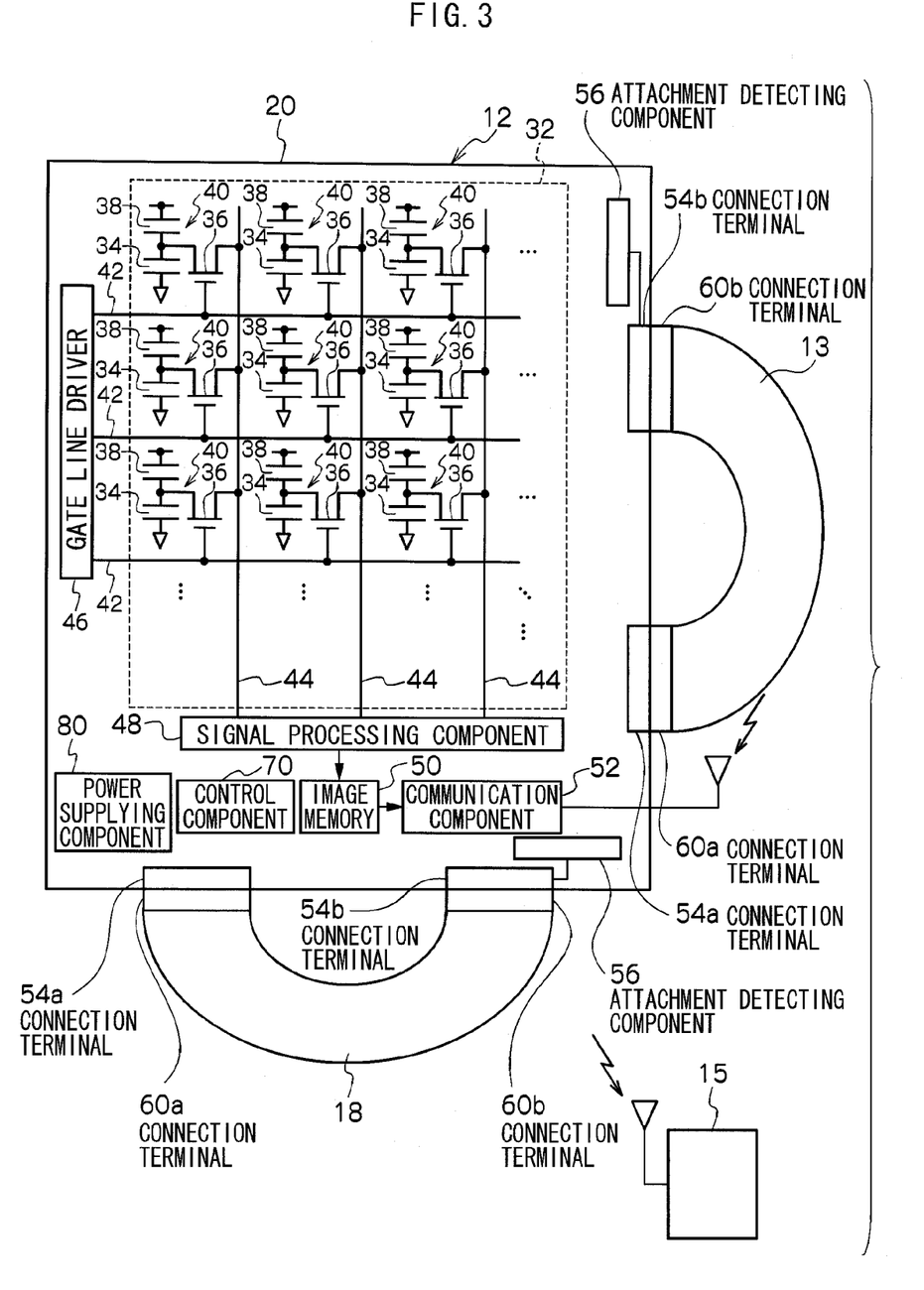
FIG. 3 is a block diagram showing the general configuration of the electronic cassette.

First, the configuration of an electronic cassette 12 pertaining to the present embodiment will be described. FIG. 1 is a general diagram showing the disposition of the electronic cassette 12 during shooting of a radiographic image. FIG. 2 is general perspective diagram showing the internal structure of the electronic cassette 12. FIG. 3 is a block diagram showing the general configuration of the electronic cassette 12.

The electronic cassette 12 pertaining to the present embodiment is portable and is capable of detecting radiation from a radiation source that has been transmitted through a subject, generating image information of a radiographic image expressed by the detected radiation, and storing the generated image information. Specifically, the electronic cassette 12 is configured as described below.

As shown in FIG. 1, the electronic cassette 12 is disposed a distance away from a radiation generating component 14 that serves as a radiation source that generates radiation during shooting of a radiographic image. The space between the radiation generating component 14 and the electronic cassette 12 at this time serves as a shooting position for a subject 16 to be positioned in. When shooting of a radiographic image is instructed, the radiation generating component 14 emits radiation of a radiation quantity corresponding to a shooting condition or the like that has been given beforehand. The radiation that has been emitted from the radiation generating component 14 carries image information as a result of being transmitted through the subject 16 positioned in the shooting position, and thereafter the electronic cassette 12 is irradiated with the radiation.

As shown in FIG. 2, the electronic cassette 12 is covered by a quadrangular flat plate-shaped casing 20 that has a predetermined thickness and comprises a material that allows radiation X to be transmitted therethrough. Inside the casing 20, there are disposed, in order from an irradiated surface 22 side of the casing 20 that is irradiated with the radiation X, a grid 24 that removes scattered radiation of the radiation X that arises in accompaniment with the radiation X being transmitted through the subject 16, a radiation detector (radiation detecting panel) 26 that serves as one example of a radiation converter that detects the radiation from the radiation source that has been transmitted through the subject 16 and converts the radiation into radiographic image information, and a lead plate 28 that absorbs back scattered radiation of the radiation X. Further, a casing 30 that houses components such as a signal processing component 48, a power supplying component 80, a control component 70, an image memory 50 and a communication component 52 (see FIG. 3) is disposed on one end side of the inside of the casing 20.

The radiation detector 26 of the electronic cassette 12 is configured as a result of a photoelectric conversion layer that absorbs and converts radiation into electric charges being laminated on a TFT active matrix substrate 32 shown in FIG. 3. The photoelectric conversion layer comprises, for example, non-crystalline a-Se (amorphous selenium) whose main component (e.g., having a content percentage equal to or greater than 50%) is selenium, and when the photoelectric conversion layer is irradiated with radiation, the photoelectric conversion layer converts the radiation with which it has been irradiated into electric charges by generating, inside of itself, electric charges (electron-hole pairs) of an electric charge quantity corresponding to the quantity of radiation with which it has been irradiated.

Further, on the TFT active matrix substrate 32, numerous pixel components 40 (in FIG. 3, the photoelectric conversion layer corresponding to the individual pixel components 40 is schematically shown as photoelectric conversion components 38) equipped with storage capacitors 34 that store the electric charges that have been generated by the photoelectric conversion layer and TFTs 36 for reading the electric charges that have been stored in the storage capacitors 34 are disposed in a matrix. The electric charges that have been generated by the photoelectric conversion layer in accompaniment with the irradiation of the electronic cassette 12 with the radiation are stored in the storage capacitors 34 of the individual pixel components 40. Thus, the radiographic image expressed by the radiation that has been transmitted through the subject and with which the electronic cassette 12 has been irradiated is converted into image information resulting from electric charges and is held in the radiation detector 26.

Further, on the TFT active matrix substrate 32, there are disposed plural gate lines 42, which extend in a constant direction (row direction) and are for switching ON and OFF the TFTs 36 of the individual pixel components 40, and plural data lines 44, which extend in a direction (column direction) orthogonal to the gate lines 42 and are for reading the stored electric charges from the storage capacitors 34 via the TFTs 36 that have been switched ON. The individual gate lines 42 are connected to a gate line driver 46, and the individual data lines 44 are connected to a signal processing component 48. When the electric charges are stored in the storage capacitors 34 of the individual pixel components 40, the TFTs 36 of the individual pixel components 40 are switched ON in order in row units by signals that are supplied via the gate lines 42 from the gate line driver 46, and the electric charges that are stored in the storage capacitors 34 of the pixel components 40 whose TFTs 36 have been switched ON are transmitted through the data lines 44 as electric charge signals and are inputted to the signal processing component 48. Consequently, the electric charges that are stored in the storage capacitors 34 of the individual pixel components 40 are read in order in row units.

The signal processing component 48 is equipped with amplifiers and sample/hold circuits that are disposed for each of the individual data lines 44, and the electric charge signals that have been transmitted through the individual data lines 44 are amplified by the amplifiers and are thereafter held in the sample/hold circuits. Further, multiplexers and A/D converters, which serve as one example of electric signal converting components that convert electric signals that include image information, are connected in order to output sides of the sample/hold circuits. The electric charge signals held in the individual sample/hold circuits are inputted in order (serially) to the multiplexers, and analog electric signals are converted into digital electric signals by the A/D converters. An image memory 50 is connected to the signal processing component 48, and the image information that has been outputted from the A/D converters of the signal processing component 48 is stored in order in the image memory 50. The image memory 50 has a storage capacity that is capable of storing image information of plural frames, and each time shooting of a radiographic image is performed, the image information obtained by the shooting is sequentially stored in the image memory 50.

Further, the electronic cassette 12 is equipped with a communication component 52 for transmitting data to and receiving data from a display device 15 by wireless communication and a control component 70 that serves as one example of a control component that controls the radiation detector 26.

The control component 70 is configured by a microcomputer that includes a CPU that controls the entire electronic cassette 12, a ROM that serves as a storage medium in which data transmitting and receiving processing programs are stored, a RAM that temporarily stores data as a work area, and a memory that serves as storage means in which various information is stored.

It will be noted that the control component is not limited to a component that controls operation of the entire device as in the present embodiment; the control component may also be a component that controls operation of part of the device.

Further, a power supplying component 80 that serves as one example of a power supplying component that supplies electrical power to at least one of the radiation detector 26 and the control component 70 is disposed in the electronic cassette 12.

The power supplying component 80 is configured to supply electrical power to the various circuits and elements in order to allow the electronic cassette 12 to operate. As the power supplying component 80, a configuration that has a built-in battery (a rechargeable secondary battery) and supplies electrical power to the various circuits and elements from the charged battery so as to not impair the portability of the electronic cassette 12 is preferable, but a primary battery may also be used as the battery, or the power supplying component 80 may also have a configuration that is always attached to a commercial power source, rectifies and transforms electrical power that has been supplied from the commercial power source, and supplies the electrical power to the various circuits and elements.

It will be noted that the power supplying component is not limited to a component that supplies electrical power to the components of the entire device as in the present embodiment; the power supplying component may also be a component that supplies electrical power to some of the components of the device. Further, the electronic cassette 12 may also have a configuration that includes plural power supplying components.

Next, the display device 15 will be described. The display device 15 is configured by a keyboard and a mouse that serve as input means, a display that serves as display means, and a PC (personal computer) that includes a CPU, a ROM and a RAM. Further, the display device 15 is equipped with a communication component for transmitting data to and receiving data from the electronic cassette 12 by wireless communication.

(Shape of Electronic Cassette 12 and Grip Portions that Attach to Electronic Cassette 12)

Next, the shape of the electronic cassette 12 and grip portions that attach to the electronic cassette 12 will be described.

The electronic cassette 12 has a shape including four sides on its periphery when seen in a planar view. Specifically, the electronic cassette 12 has a quadrangular shape (see FIG. 3 and FIG. 4). More specifically, the electronic cassette 12 has a rectangular shape. It will be noted that the electronic cassette 12 may also have a shape where its corners are rounded.

It will be noted that the detection region of the radiation detector 26 that detects the radiation is also configured to have the same shape as that of the electronic cassette 12. The detection region is configured to have a rectangular shape whose long sides are disposed along the long sides of the electronic cassette 12 that has a rectangular shape. It will be noted that the detection region may also be configured to have a rectangular shape whose short sides are disposed along the long sides of the electronic cassette 12 that has a rectangular shape.

Figure 4:
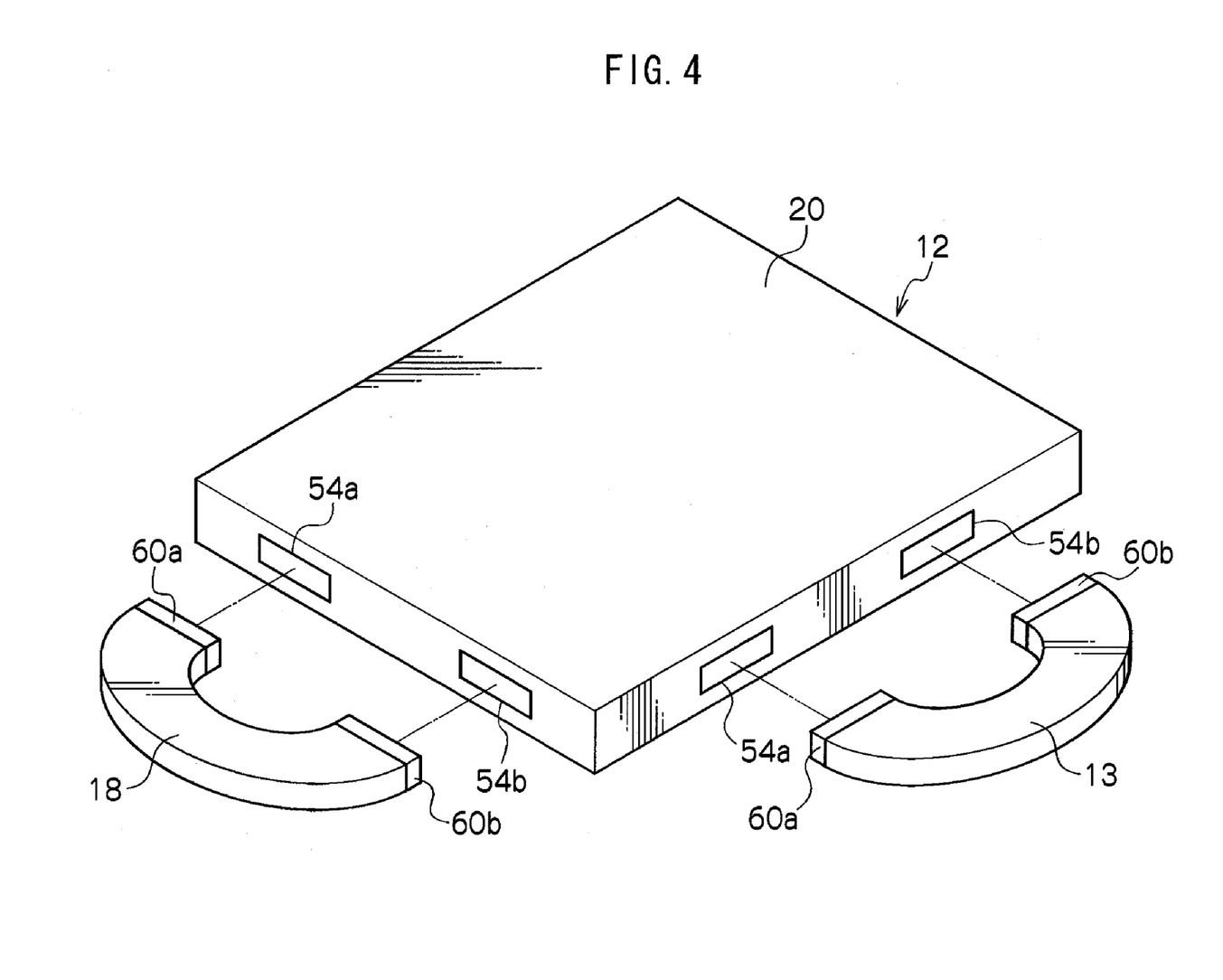
FIG. 4 is a perspective diagram showing the exterior of the electronic cassette and handles.

Further, as shown in FIG. 4, a handle 13 and a handle 18 for carrying the electronic cassette 12 are, as one example of grip portions that are capable of being gripped by a person handling the electronic cassette 12, disposed on the casing 20 of the electronic cassette 12.

The handle 13 and the handle 18 are disposed respectively on side surfaces that configure mutually adjacent sides of the electronic cassette 12 that has a rectangular shape when seen in a planar view. The handle 18 is attached to a short side of the electronic cassette 12, and the handle 13 is attached to a long side of the electronic cassette 12. Thus, the handle 13 is disposed in a position whose orientation differs 90 degrees with respect to the handle 18.

The handle 13 and the handle 18 each include connection terminals 60*a* and 60*b* for attaching to the electronic cassette 12. The electronic cassette 12 includes connection terminals 54*a* and 54*b* to which the connection terminals 60*a* and 60*b* of the handle 13 and the handle 18 detachably connect. Thus, the handle 13 and the handle 18 are configured to be attachable to and detachable from the electronic cassette 12 and function as handles in a state where they have been attached to the electronic cassette 12.

It will be noted that the handle 13 and the handle 18 may also be configured such that just one of the handle 13 and the handle 18 is detachable, or, the handle 13 and the handle 18 may also be configured such that they cannot be detached from the electronic cassette 12.

Further, the handle 13 and the handle 18 are configured to be U-shaped. It will be noted that the grip portions may also be T-shaped or square U-shaped or have a shape with a hole such as a round shape; it suffices as long as they have shapes that function as grip portions. Further, the electronic cassette 12 may also have a configuration where three or more of the plural grip portions are disposed. Further, the electronic cassette 12 may also have a configuration where the handle 13 and the handle 18 are disposed on opposite sides of the four sides or can be configured such that the handle 13 and the handle 18 are disposed in different orientations. Further, the handle 13 and the handle 18 may also be disposed on the same side of the four sides (see FIG. 13).

Moreover, the grip portions may also have a configuration that is not penetrated, that is, a configuration that does not include a space for a person handling the electronic cassette 12 to insert his/her hand (part of the hand, such as the fingers); for example, the grip portions may be ones where recessed portions for a person handling the electronic cassette 12 to catch onto with his/her hand (part of the hand, such as the fingers) are formed or may be ones on which grippable convex portions are formed.

Figure 5:
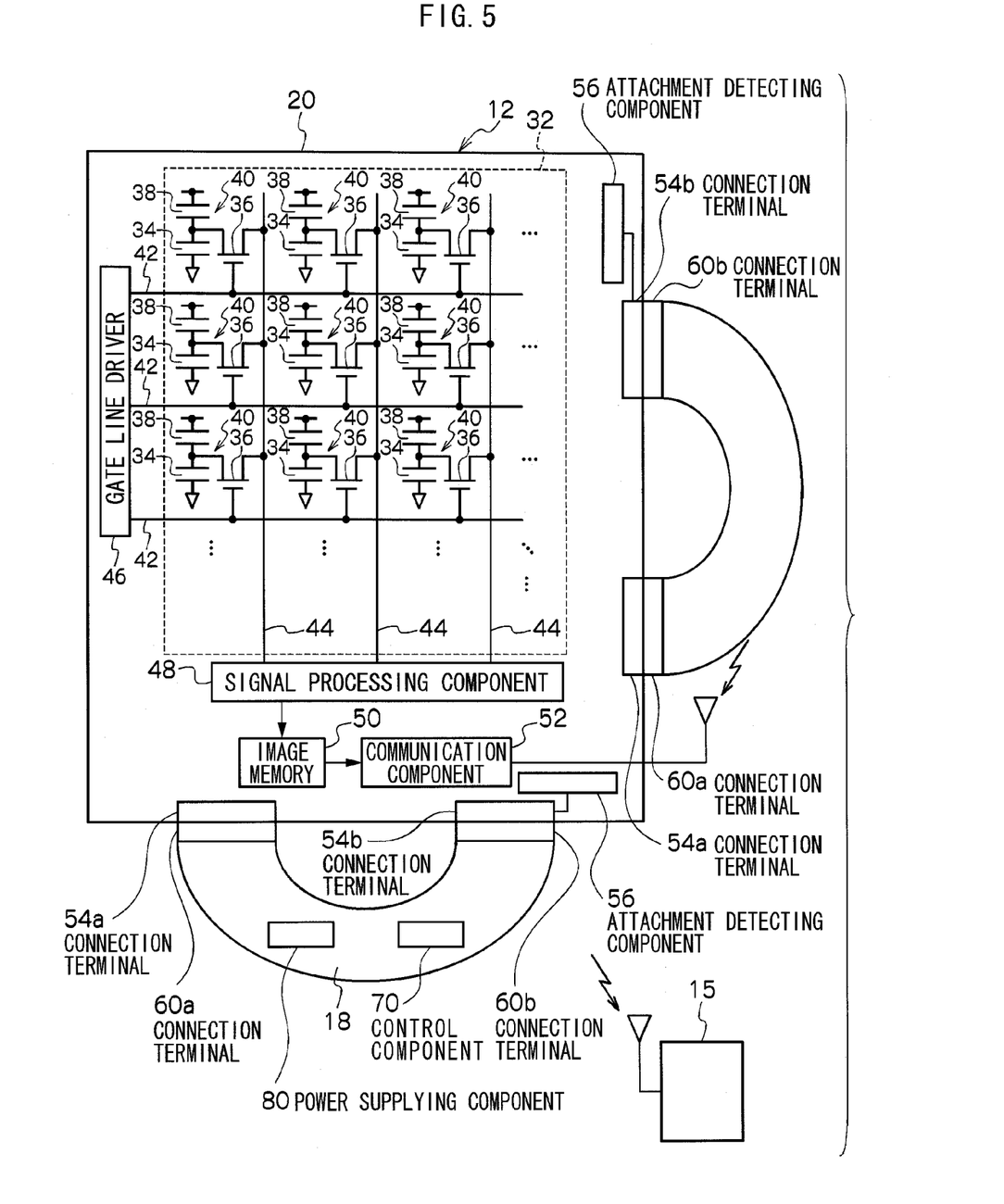
FIG. 5 is a diagram showing a configuration where a control component and a power supplying component are disposed in a handle of the electronic cassette.
Figure 6:
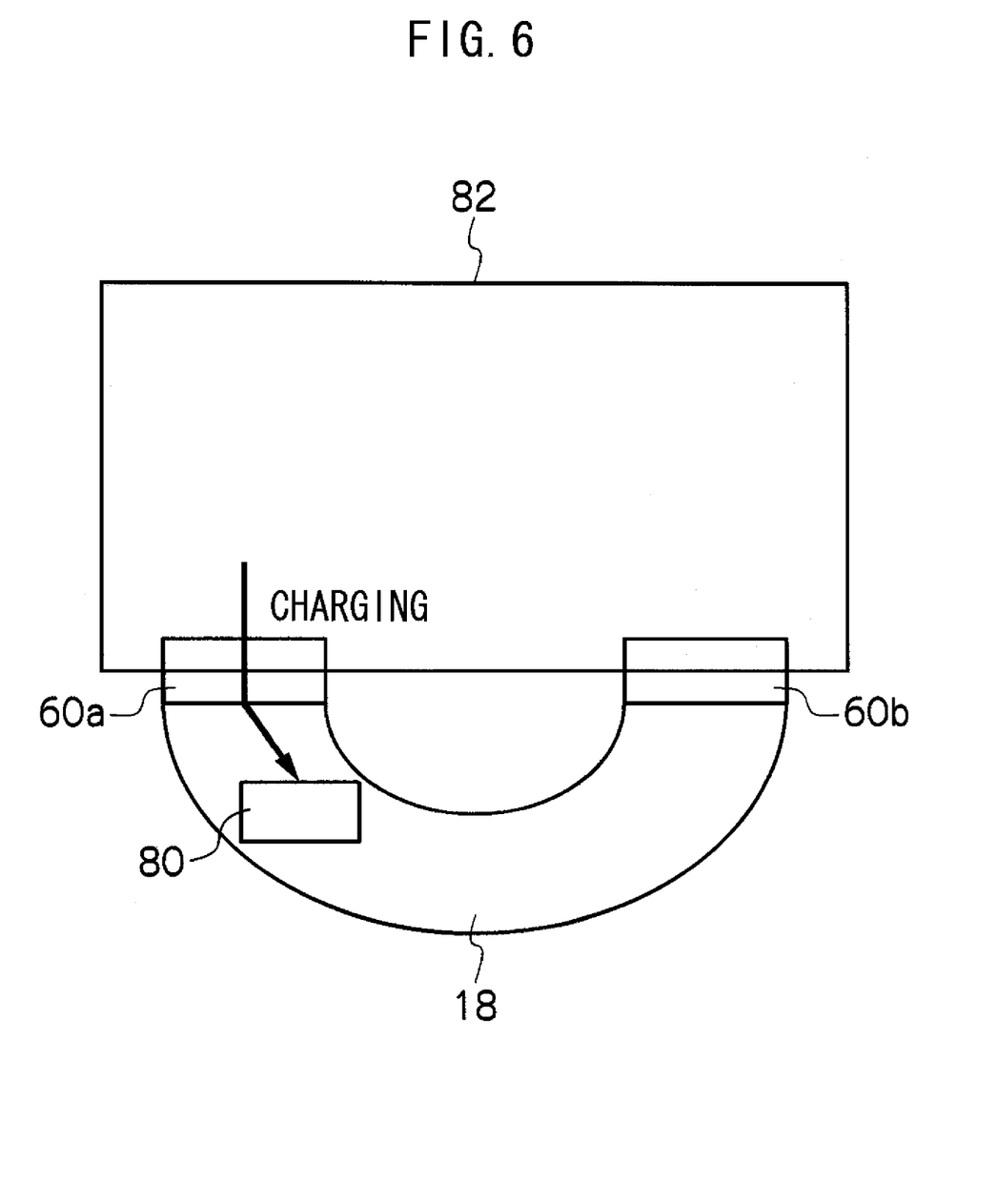
FIG. 6 is a diagram showing a state where a handle of the electronic cassette has been attached to a charger.

Further, as shown in FIG. 5, the power supplying component 80 and the control component 70 may also be disposed in the handle 13 and the handle 18 rather than in the body of the electronic cassette 12. FIG. 5 shows a configuration where both the power supplying component 80 and the control component 70 are integrated with the handle 18. By disposing the power supplying component 80 in the handle 18, as shown in FIG. 6, it becomes possible to detach the handle 18 from the electronic cassette 12, attach the handle 18 to a charger 82, and charge the handle 18.

It will be noted that both the power supplying component 80 and the control component 70 may also be disposed in the handle 13. Further, the electronic cassette 12 may also be configured such that one of the power supplying component 80 and the control component 70 is disposed in the handle 13 and such that the other of the power supplying component 80 and the control component 70 is disposed in the handle 18. Further, either one of the power supplying component 80 or the control component 70 may be disposed in either one of the handle 13 or the handle 18.

Moreover, as long as the component is one other than the component configuring the radiation detection region that detects the radiation (specifically, the radiation detector 26), it is possible to dispose that component in at least one of the handle 13 and the handle 18.

Figure 7:
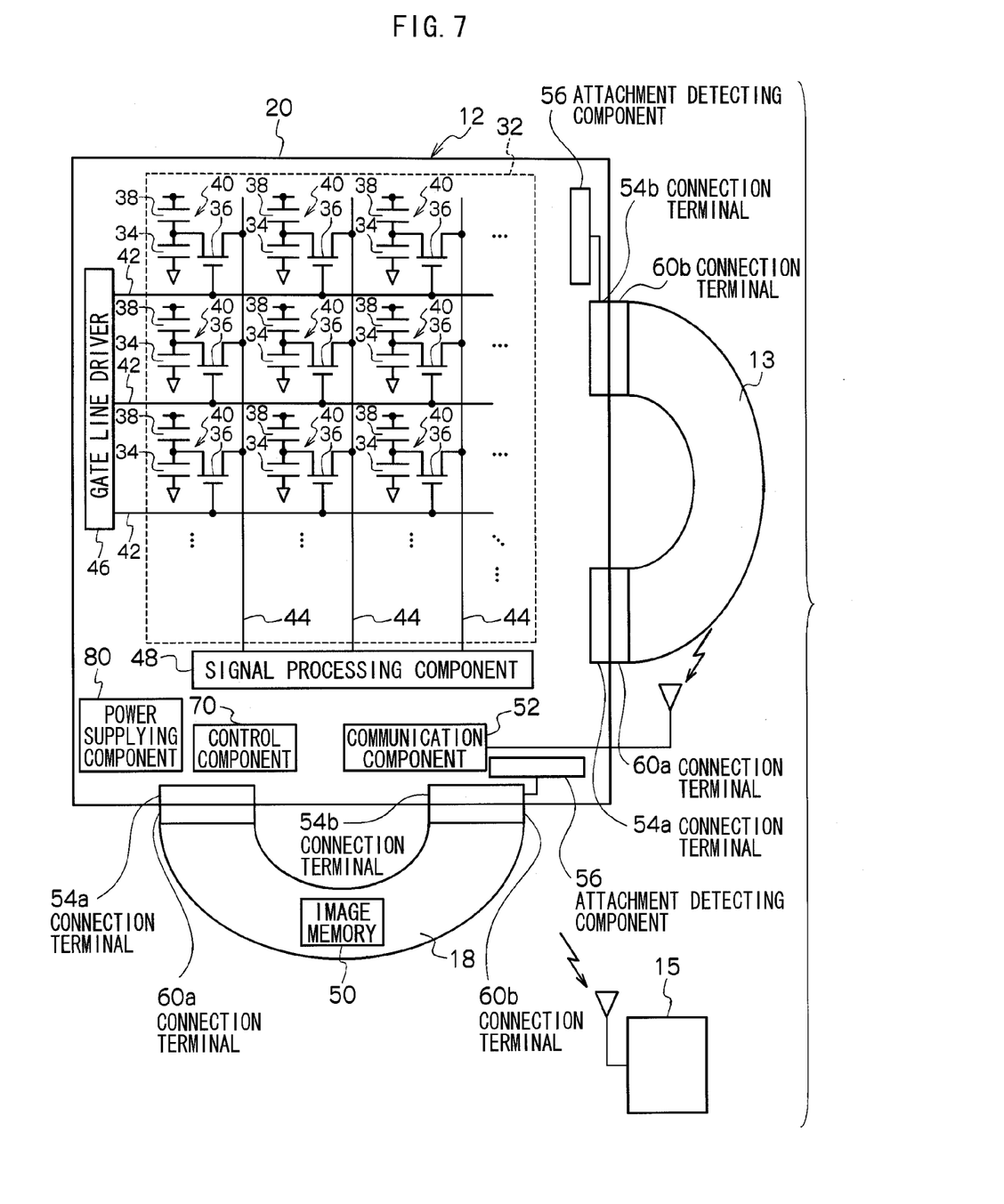
FIG. 7 is a diagram showing a configuration where an image memory is disposed in a handle of the electronic cassette.
Figure 8:
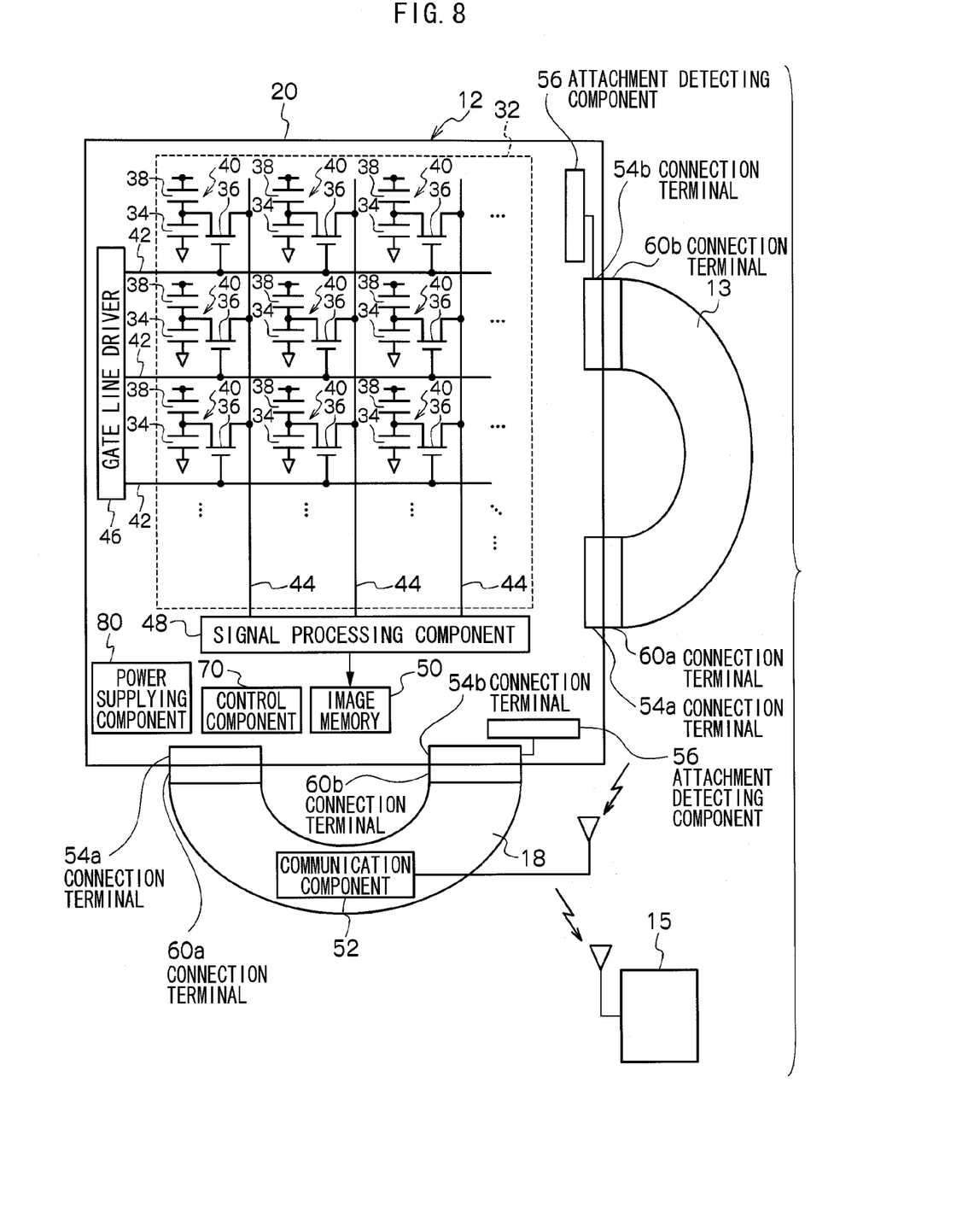
FIG. 8 is a diagram showing a configuration where a communication component is disposed in a handle of the electronic cassette.

Consequently, as shown in FIG. 7, the image memory 50 can be disposed in the handle 18, or, as shown in FIG. 8, the communication component 52 can be disposed in the handle 18.

Moreover, when the handle 13 and the handle 18 are disposed in a positional relationship where they are orthogonal to each other, the handle 13 or the handle 18 in which a component other than the component configuring the radiation detection region that detects the radiation (specifically, the radiation detector 26) is installed can be disposed in proximity to the signal processing component 48 and wires can be shortened from whichever position, which is a preferable configuration from the standpoint of countering electromagnetic waves.

Further, the electronic cassette 12 may also be configured such that an ID storing ROM, in which is stored a display device ID that discriminates the display device 15 and is used in order to identify between which electronic cassette 12 and which display device 15 communication is to be performed, is disposed in at least one of the handle 13 and the handle 18. Because of this configuration, the data transmission and reception destination display device 15 can be identified by attaching the handle in which information of the display device ID is stored to the electronic cassette 12 and acquiring the display device ID from the handle. When seen from the display device 15 side, the electronic cassette 12 to which the handle in which the information of its own display device ID is stored has been attached can be identified as the communication destination electronic cassette 12.

Moreover, the electronic cassette 12 may also have a configuration where a memory that stores a shooting condition when shooting a radiographic image, information of a patient who becomes the subject 16 and various information such as an electronic cassette ID is disposed in at least one of the handle 13 and the handle 18.

(Relationship Between Attachment Situation of Handle 13 and Handle 18 and Image Processing)

Next, the relationship between the attachment situation of the handle 13 and the handle 18 and image processing will be described.

The electronic cassette 12 includes attachment detecting components 56 that detect whether or not the handle 13 and the handle 18 are attached to the electronic cassette 12.

The attachment detecting components 56 are configured to be electrically connected when, for example, the connection terminals 60*a* and 60*b* are connected to the connection terminals 54*a* and 54*b*, and the attachment detecting components 56 detect whether or not the handle 13 and the handle 18 are attached to the electronic cassette 12 depending on whether or not electricity is flowing between the connection terminals 60*a* and 60*b* and the connection terminals 54*a* and 54*b*.

It will be noted that the attachment detecting components 56 may also be configured to detect whether or not the handle 13 and the handle 18 are attached to the electronic cassette 12 utilizing light such as infrared light or an electrostatic effect (e.g., a method that detects, by capacitance, whether or not a dielectric is near).

The electronic cassette 12 pertaining to the present embodiment is configured such that the control component 70 changes, on the basis of the detection results that the attachment detecting components 56 have detected, the image processing content of the image information that has been converted by the radiation detector 26.

For example, in a configuration where the attachment position of the handle changes depending on the orientation in which the electronic cassette 12 is loaded into a shooting table, the electronic cassette 12 can be configured to change the orientation of the image information on the basis of the detection results that the attachment detecting components 56 have detected.

Figure 9:
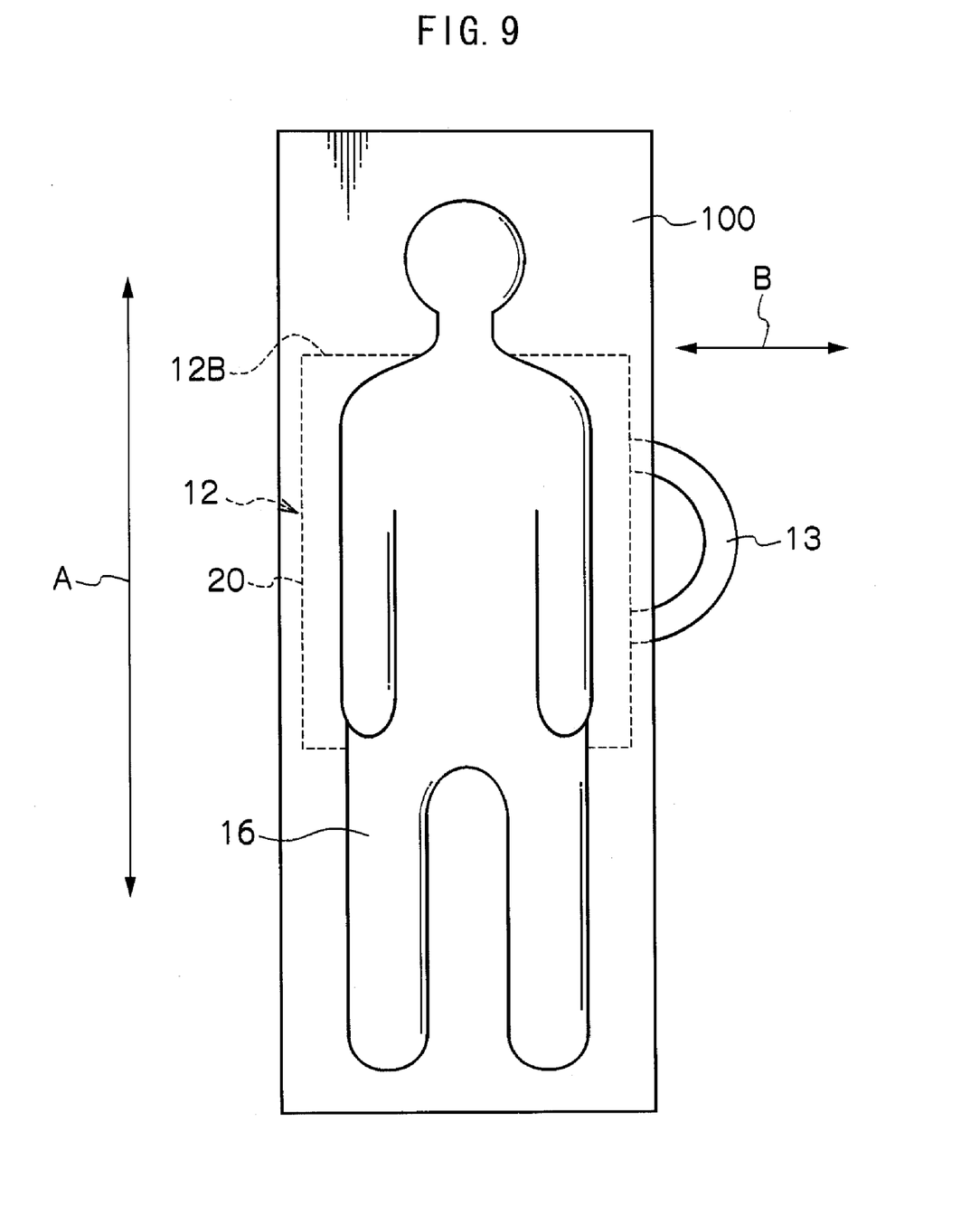
FIG. 9 is a diagram showing a state where the electronic cassette has been vertically loaded into a shooting table.
Figure 10:
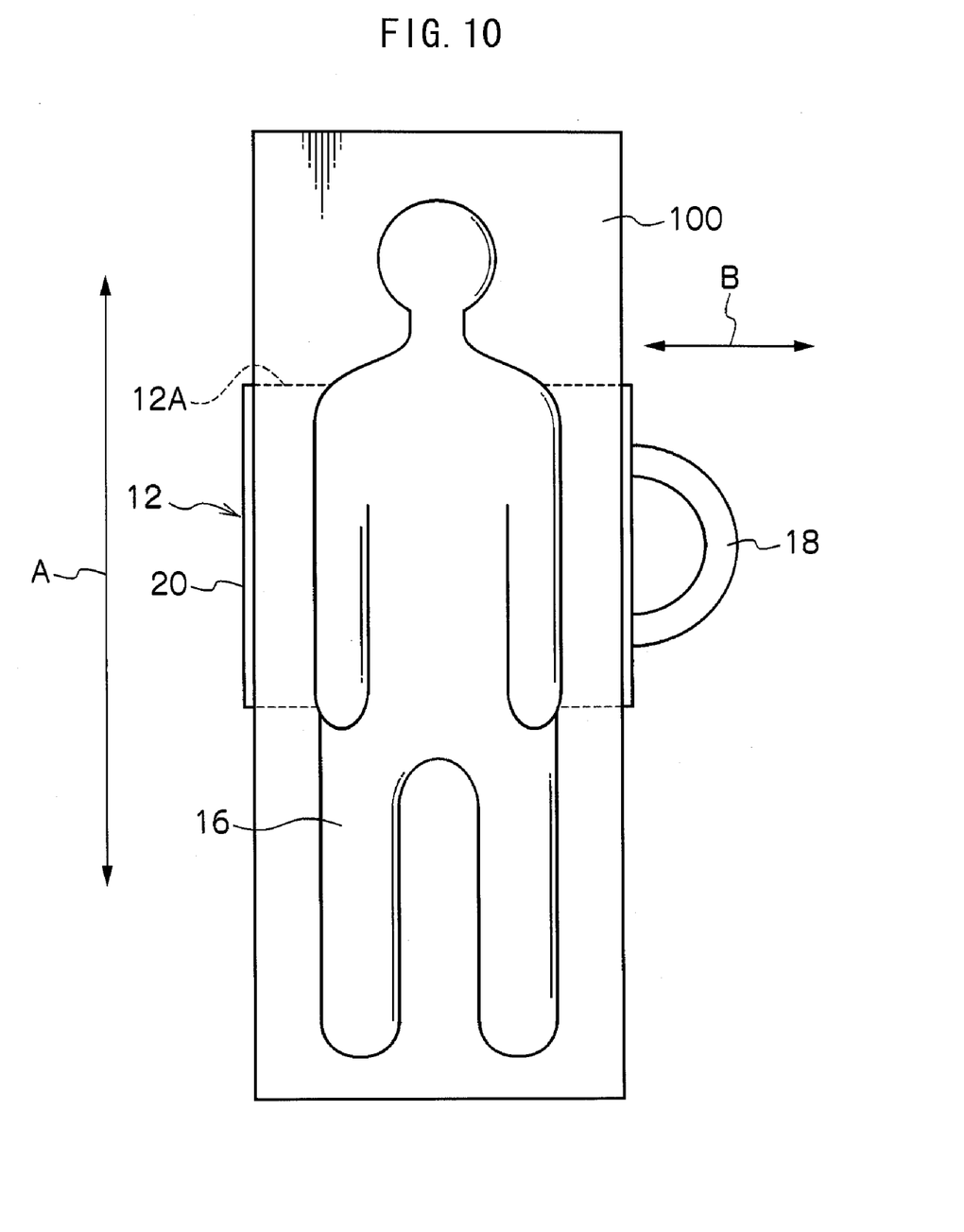
FIG. 10 is a diagram showing a state where the electronic cassette has been horizontally loaded into the shooting table.

A specific configuration of this configuration will be described below. As shown in FIG. 9 and FIG. 10, a shooting table 100 is, for example, configured as a bed on which an examinee that becomes the subject 16 can lie down, and the shooting table 100 is for shooting an examinee who is lying down. It will be noted that the shooting table 100 may also be for shooting an examinee who is standing.

The electronic cassette 12 is configured such that it can be loaded into this shooting table 12. The electronic cassette 12 is inserted and loaded into the shooting table 100 along an orthogonal direction (direction of arrow B in FIG. 9 and FIG. 10) that is orthogonal to the head-to-foot direction (direction from the head to the feet; direction of arrow A in FIG. 9 and FIG. 10) of an examinee who is lying on the shooting table 100, and the electronic cassette 12 is removed and unloaded from the shooting table 100 in the opposite direction of that insertion direction.

Further, the electronic cassette 12 is configured such that the electronic cassette 12 can be loaded into the shooting table 100 such that the long direction of the electronic cassette 12 is along the head-to-foot direction of an examinee who is lying on the shooting table 100 (see FIG. 9). This way of loading will hereinafter be called vertical loading.

Further, the electronic cassette 12 is configured such that the electronic cassette 12 can be loaded into the shooting table 100 such that the short direction of the electronic cassette 12 is along the head-to-foot direction of an examinee who is lying on the shooting table 100 (see FIG. 10). This way of loading will hereinafter be called horizontal loading.

In this configuration, the radiation generating component 14 is disposed above the shooting table 100, and the examinee is disposed between the radiation generating component 14 and the electronic cassette 12 (the shooting table 100).

The radiation from the radiation generating component 14 is transmitted through the examinee who is lying on the shooting table 100, and the electronic cassette 12 that has been loaded into the shooting table 100 is irradiated with that radiation. Thus, the examinee is imaged.

Here, when the electronic cassette 12 is to be vertically loaded, the electronic cassette 12 cannot be loaded into the shooting table 100 in a state where the handle 18 that attaches to a short side of the electronic cassette 12 is attached to the electronic cassette 12. This is because, for example, the handle 18 that is attached to the electronic cassette 12 touches the edge of the insertion opening through which the electronic cassette 12 is inserted into the shooting table 100.

Further, when the electronic cassette 12 is to be horizontally loaded, the electronic cassette 12 cannot be loaded into the shooting table 100 in a state where the handle 13 that attaches to a long side of the electronic cassette 12 is attached to the electronic cassette 12. This is because, for example, the handle 13 that is attached to the electronic cassette 12 touches the edge of the insertion opening through which the electronic cassette 12 is inserted into the shooting table 100.

Further, the electronic cassette 12 is configured such that it is not actuated unless at least one of the handle 13 and the handle 18 is attached to the electronic cassette 12. For example, imaging operation of the electronic cassette 12 stops when the supply of electrical power from the power supplying component 80 stops. It will be noted that the electronic cassette 12 may also be configured to stop the irradiation with radiation by the radiation generating component 14. Further, the electronic cassette 12 may also be configured to notify and prompt an operator to attach either the handle 13 or the handle 18 to the electronic cassette 12.

Thus, when the electronic cassette 12 is to be loaded into the shooting table 100 and shooting is to be performed, the electronic cassette 12 is vertically loaded when the handle 13 is attached to the electronic cassette 12.

Further, when the electronic cassette 12 is to be loaded into the shooting table 100 and shooting is to be performed, the electronic cassette 12 is horizontally loaded when the handle 18 is attached to the electronic cassette 12.

The control component 70 is, in regard to an image that has been shot in a state where the handle 13 is attached, configured to store in the image memory an image where a short side 12B of the electronic cassette 12 positioned on the head side of the examinee is on top.

Thus, when an image that has been imaged by the electronic cassette 12 is to be displayed on the display device, an image where the short side 12B is on top is displayed, and when an image that has been imaged by the electronic cassette 12 is to be recorded in a recording medium, an image where the short side 12B is on top is recorded.

Further, the control component 70 is, in regard to an image that has been shot in a state where the handle 18 is attached, configured to store in the image memory an image where a long side 12A of the electronic cassette 12 positioned on the head side of the examinee is on top. That is, an image obtained by rotating 90 degrees an image where the short side 12B is on top is stored.

Thus, when an image that has been imaged by the electronic cassette 12 is to be displayed on the display device, an image where the long side 12A is on top is displayed, and when an image that has been imaged by the electronic cassette 12 is to be recorded in a recording medium, an image where the long side 12A is on top is recorded.

It will be noted that, in a configuration where, for example, just the handle 18 of the handle 13 and the handle 18 is detachable, when the electronic cassette 12 is to be vertically loaded, the electronic cassette 12 is loaded into the shooting table 100 in a state where just the handle 13 is attached to the electronic cassette 12, and when the electronic cassette 12 is to be horizontally loaded, the electronic cassette 12 is loaded into the shooting table 100 in a state where both the handle 13 and the handle 18 are attached to the electronic cassette 12; thus, processing of images corresponding to the attachment situation of the handles becomes possible.

Further, rather than performing image processing when storing an image in the image memory, the electronic cassette 12 may also be configured to process an image such as when displaying an image and when recording an image.

Consequently, for example, the electronic cassette 12 may send image information and attachment information of the handle 13 and the handle 18 to an external device such as the display device, and the display device may perform image processing.

(Action of Electronic Cassette 12 Pertaining to Present Embodiment)

Next, the action of the electronic cassette 12 pertaining to the present embodiment will be described.

Figure 11:
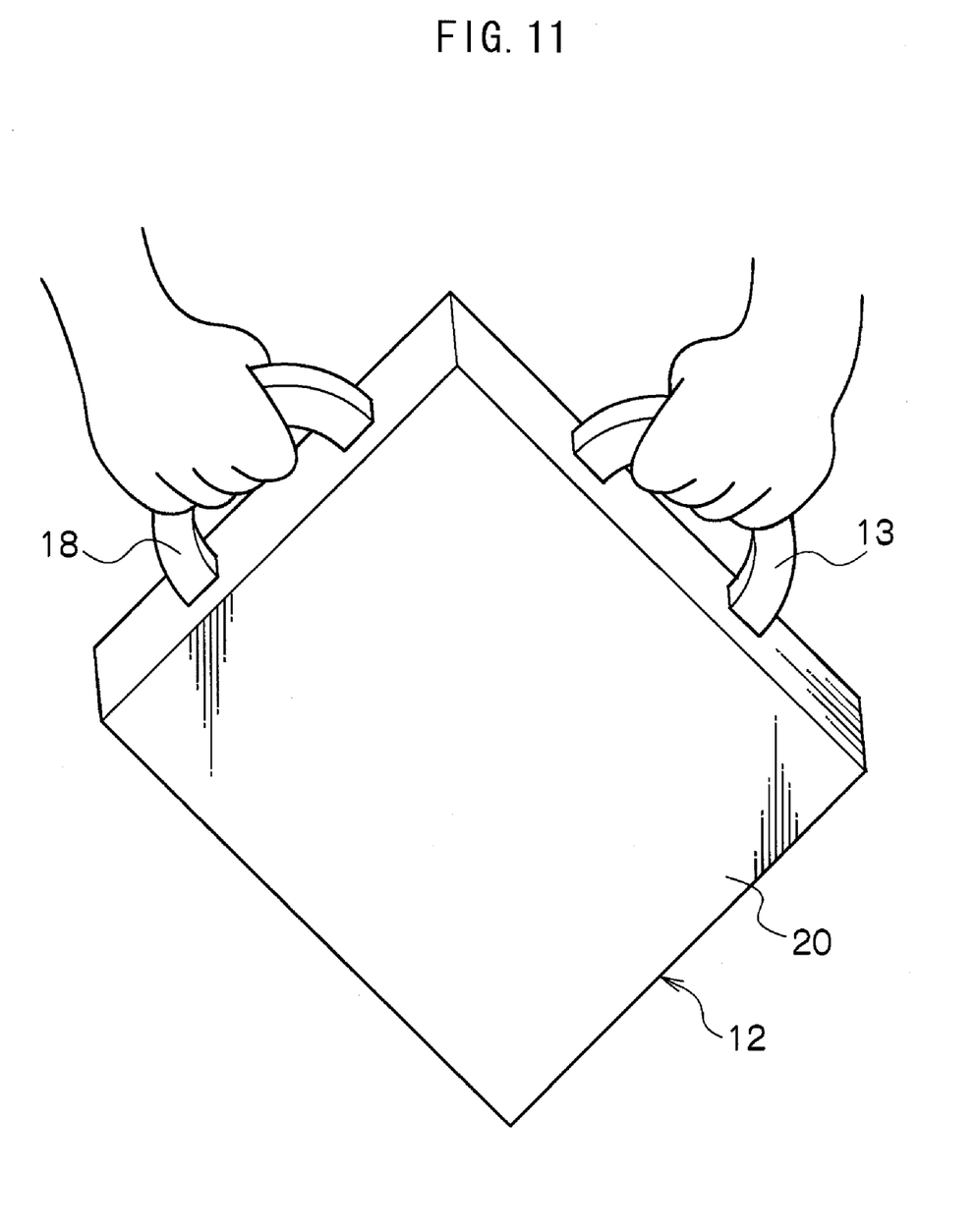
FIG. 11 is a diagram showing a person gripping two handles of the electronic cassette and carrying the electronic cassette.

In the electronic cassette 12 pertaining to the present embodiment, the handle 13 and the handle 18 are disposed, so a person handling the electronic cassette 12 can grip the handle 13 and the handle 18 and carry the electronic cassette 12 as shown in FIG. 11. Thus, the person can grip and carry the electronic cassette 12 while dispersing the weight of the electronic cassette 12, so carrying the electronic cassette becomes easy.

Figure 13:
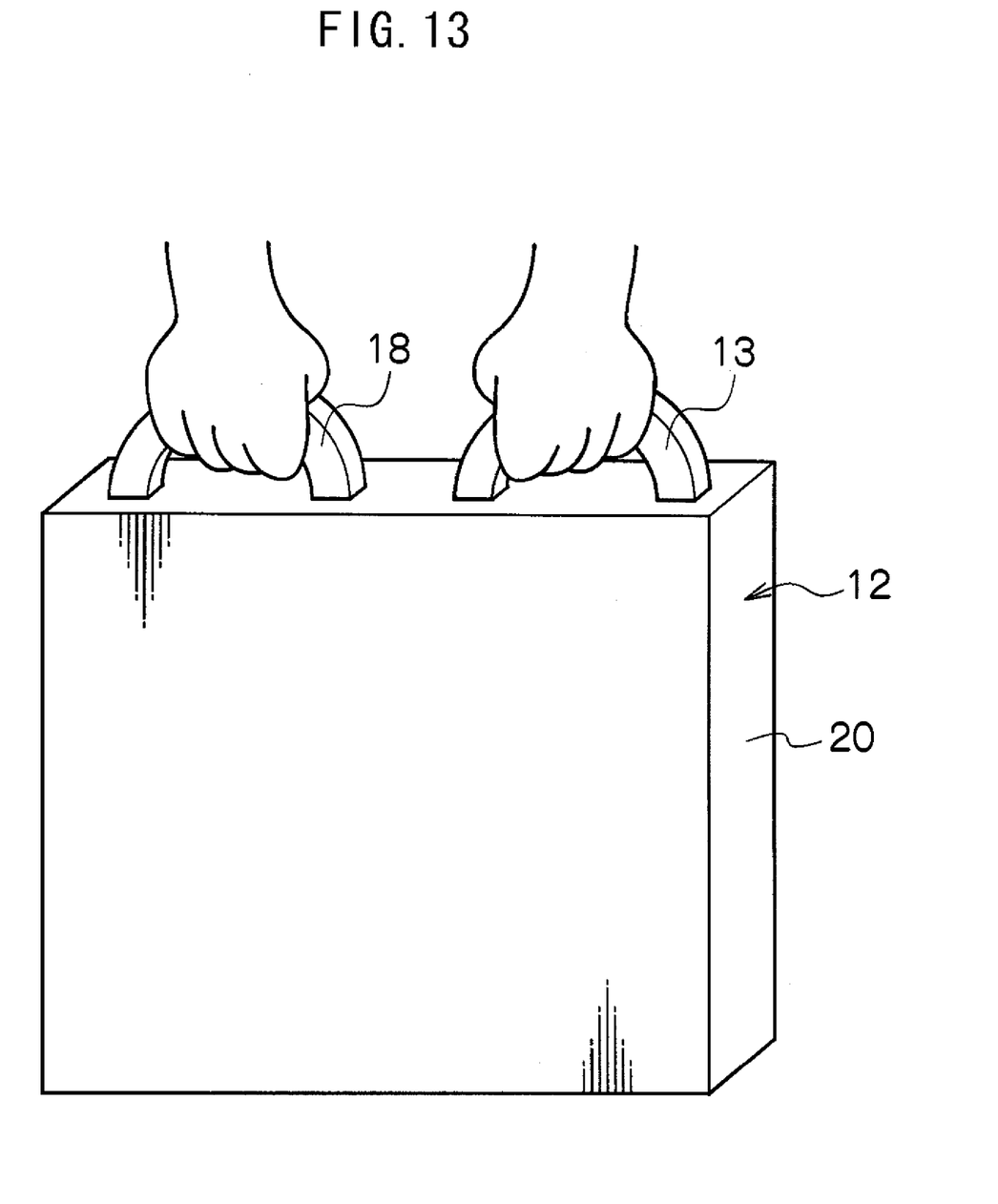
FIG. 13 is a diagram showing a configuration where two handles are disposed on the same side of the electronic cassette.

At this time, the handle 13 and the handle 18 may be disposed on the same side as shown in FIG. 13. By disposing the handle 13 and the handle 18 in this manner, it becomes easier for two people to carry the electronic cassette 12.

Further, when the person loads the electronic cassette 12 into the shooting table 100 or the like, the person can grip either the handle 13 or the handle 18 and load the electronic cassette 12.

Further, because the handle 13 and the handle 18 can be detached, the person can detach the unnecessary handle 13 and handle 18 when carrying the electronic cassette 12, and it becomes easier for the person to carry the electronic cassette 12 without the handle 13 and the handle 18 getting in the way.

Further, the person carrying the electronic cassette 12 can select, from the handle 13 and the handle 18, the handle with which it is easier to handle the electronic cassette 12 and can attach the selected handle to and carry the electronic cassette 12.

Figure 12A:
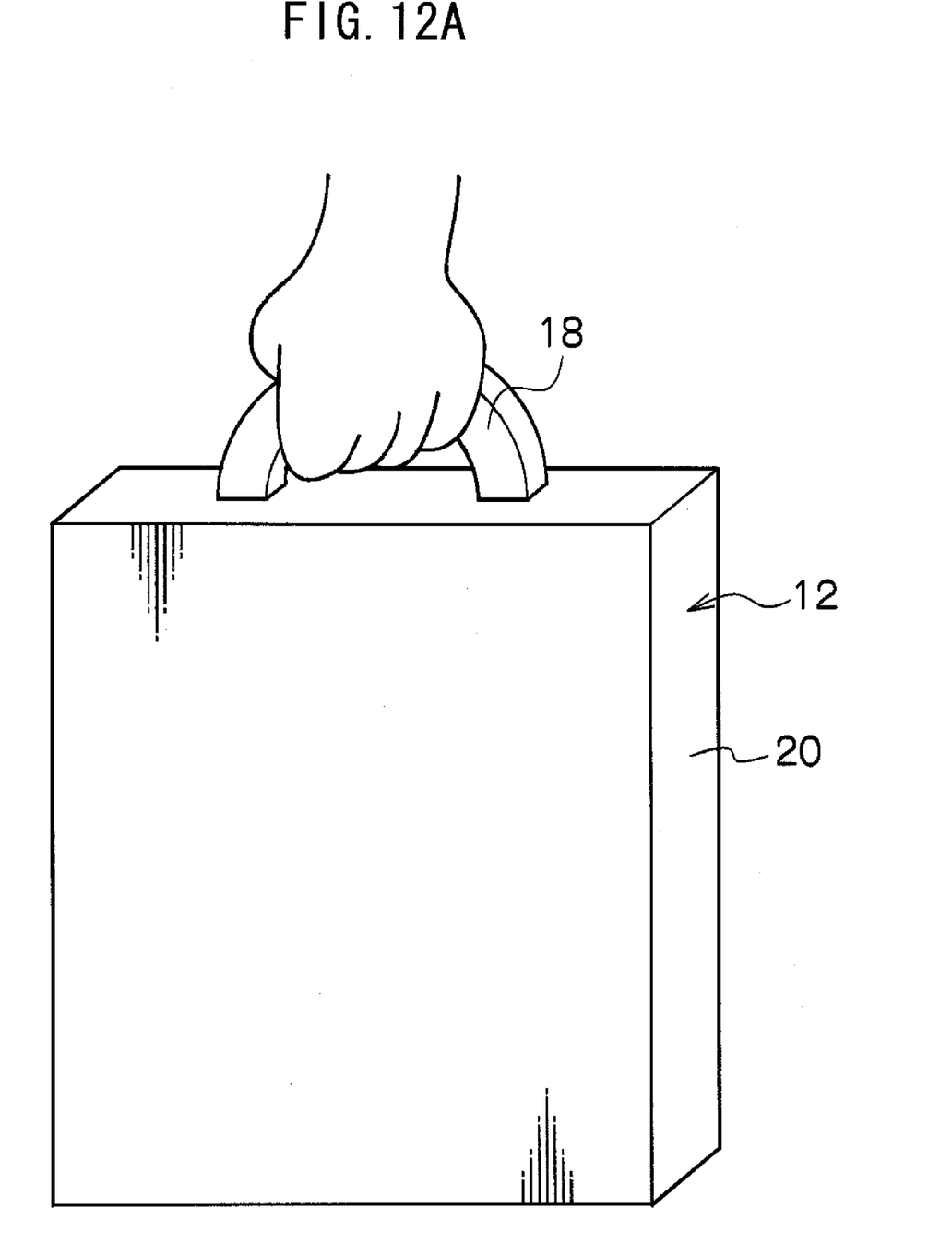
FIG. 12A and FIG. 12B are diagrams showing a person attaching either one of the two handles of the electronic cassette, gripping that handle and carrying the electronic cassette, with FIG. 12A showing a case where the person has attached a handle that is on a short side of the electronic cassette and FIG. 12B showing a case where the person has attached a handle that is on a long side of the electronic cassette.
Figure 12B:
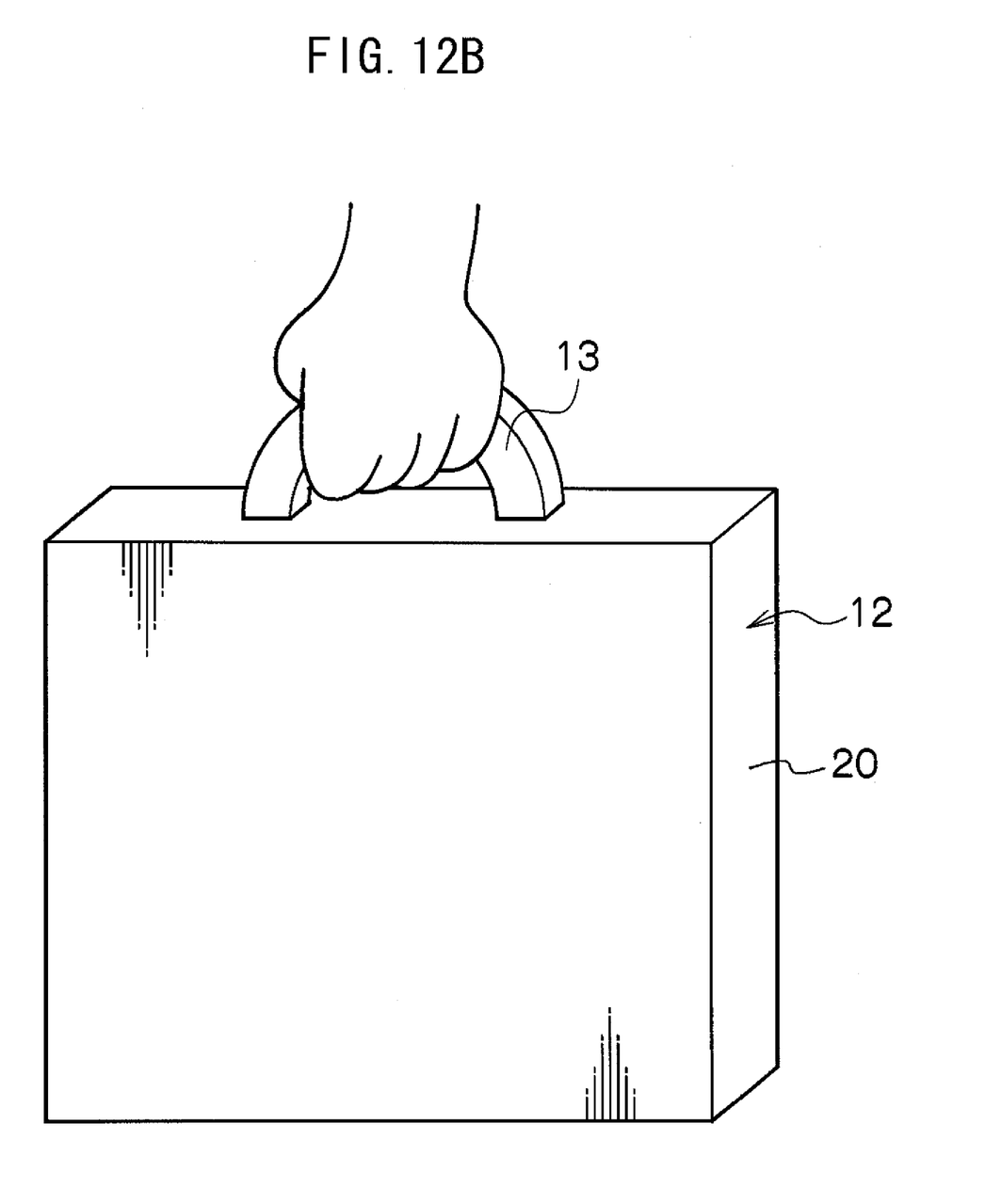

For example, it is conceivable that it is easier for a tall person to handle the electronic cassette 12 by attaching the handle 18 and carrying the electronic cassette 12 such that, as shown in FIG. 12A, the long sides of the electronic cassette 12 become upright and that it is easier for a short person to handle the electronic cassette 12 by attaching the handle 13 and carrying the electronic cassette 12 such that, as shown in FIG. 12B, the short sides of the electronic cassette 12 become upright. Further, it is conceivable that, when the person handling the electronic cassette 12 carries the electronic cassette 12 through a narrow corridor or a corridor where there are many people, it is easier for that person to handle the electronic cassette 12 by attaching the handle 18 and carrying the electronic cassette 12 such that the long sides of the electronic cassette 12 become upright.

Further, by disposing the power supplying component 80 and the control component 70 in the handle 13 and in the handle 18, handling of the electronic cassette 12 during maintenance, upgrading or charging becomes easier. Further, by disposing the power supplying component 80 in the handle 18, as shown in FIG. 6, it becomes possible to detach the handle 18 from the electronic cassette 12, attach the handle 18 to the charger 82, and charge the handle 18. Thus, handling of the electronic cassette 12 during charging becomes easy, and the charger 82 itself can also be made compact.

Moreover, when the electronic cassette 12 pertaining to the present embodiment is to be vertically loaded into the shooting table 100, the operator can grip the handle 13 and load the electronic cassette 12 into the shooting table 100 in a state where the handle 13 is attached to a long side of the electronic cassette 12. In regard to an image that has been shot in a state where the handle 13 is attached, the control component 70 stores, in the image memory, an image where the short side 12B of the electronic cassette 12 positioned on the head side of the examinee is on top.

Further, when the electronic cassette 12 pertaining to the present embodiment is to be horizontally loaded into the shooting table 100, the operator can grip the handle 18 and load the electronic cassette 12 into the shooting table 100 in a state where the handle 18 is attached to a short side of the electronic cassette 12. In regard to an image that has been shot in a state where the handle 18 is attached, the control component 70 stores, in the image memory, an image where the long side 12A of the electronic cassette 12 positioned on the head side of the examinee is on top.

The orientation of the image of the image information changes depending on the attachment situation of the handle 13 and the handle 18 in this manner, so it becomes unnecessary to separately perform operation to change the orientation of the image of the image information.

As described above, according to the configuration of the present embodiment, handling of the electronic cassette 12 becomes easy. The present invention is not limited to the preceding embodiment, and various modifications, changes and improvements are possible.

What is claimed is:

1. An electronic cassette comprising:
   a casing;
   a radiation converter that is housed inside the casing, detects radiation from a radiation source that has been transmitted through a subject, and converts the radiation into radiographic image information;
   a control component that controls the radiation converter;
   a power supplying component that supplies electrical power to at least one of the radiation converter and the control component; and
   plural grip portions that are disposed on the casing, wherein
   at least one of the plural grip portions is detachable, and the electronic cassette further comprises an attachment detecting component that detects whether or not the at least one grip portion that is detachable is attached, wherein the control component performs, on the basis of the detection result that the attachment detecting component has detected, image processing that changes the orientation of the radiographic image information that the radiation converter has converted.

2. The electronic cassette according to claim 1, wherein at least one of the control component and the power supplying component is integrated with the at least one grip portion that is detachable.

3. The electronic cassette according to claim 1, wherein the at least one grip portion that is detachable is disposed so as to identify, when the electronic cassette is to be loaded into a shooting table, the loading direction with respect to the shooting table.

4. The electronic cassette according to claim 1, wherein the at least one grip portion that is detachable is disposed such that, when the electronic cassette is to be loaded into a shooting table in one loading direction, the at least one grip portion that is detachable touches part of the shooting table so that further loading in the loading direction is restricted.

5. The electronic cassette according to claim 1, wherein the electronic cassette includes side surfaces that are perpendicular to a substantially rectangular surface as seen in a planar view that receives the radiation, and the plural grip portions are respectively disposed on the side surfaces which are different.

6. The electronic cassette according to claim 1, wherein the plural grip portions are disposed in a mutually orthogonal orientation.

* * * * *